(12) United States Patent
Ko et al.

(10) Patent No.: US 9,526,787 B2
(45) Date of Patent: Dec. 27, 2016

(54) SUSTAINED-RELEASE LIPID PRE-CONCENTRATE OF PHARMACOLOGICALLY ACTIVE SUBSTANCE AND PHARMACEUTICAL COMPOSITION COMPRISING THE SAME

(75) Inventors: Jin Young Ko, Seoul (KR); Ji Yeon Kim, Seoul (KR); So Hyun Park, Seoul (KR); Sung Won An, Seoul (KR); Min Hyo Ki, Seoul (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 14/241,696

(22) PCT Filed: Aug. 28, 2012

(86) PCT No.: PCT/KR2012/006855
§ 371 (c)(1),
(2), (4) Date: Feb. 27, 2014

(87) PCT Pub. No.: WO2013/032207
PCT Pub. Date: Mar. 7, 2013

(65) Prior Publication Data
US 2014/0206616 A1    Jul. 24, 2014

(30) Foreign Application Priority Data

Aug. 30, 2011 (KR) .................. 10-2011-0087160

(51) Int. Cl.
| | |
|---|---|
| *A61K 38/00* | (2006.01) |
| *A61K 47/22* | (2006.01) |
| *A61K 9/00* | (2006.01) |
| *A61K 47/24* | (2006.01) |
| *A61K 47/26* | (2006.01) |
| *A61K 9/107* | (2006.01) |
| *A61K 31/18* | (2006.01) |
| *A61K 31/58* | (2006.01) |
| *A61K 31/713* | (2006.01) |
| *A61K 38/26* | (2006.01) |
| *A61K 47/10* | (2006.01) |
| *A61K 47/14* | (2006.01) |
| *A61K 48/00* | (2006.01) |

(52) U.S. Cl.
CPC .............. *A61K 47/22* (2013.01); *A61K 9/0019* (2013.01); *A61K 9/0024* (2013.01); *A61K 9/1075* (2013.01); *A61K 31/18* (2013.01); *A61K 31/58* (2013.01); *A61K 31/713* (2013.01); *A61K 38/26* (2013.01); *A61K 47/10* (2013.01); *A61K 47/14* (2013.01); *A61K 47/24* (2013.01); *A61K 47/26* (2013.01); *A61K 48/0016* (2013.01)

(58) Field of Classification Search
CPC ...... A61K 31/18; A61K 31/58; A61K 31/713; A61K 38/26; A61K 47/10; A61K 47/14; A61K 47/22; A61K 47/24; A61K 47/26; A61K 48/0016; A61K 9/0019; A61K 9/1075

See application file for complete search history.

(56) References Cited

U.S. PATENT DOCUMENTS

| | | | |
|---|---|---|---|
| 4,816,553 A | 3/1989 | Baur | 528/245 |
| 5,480,656 A | 1/1996 | Okada et al. | |
| 5,807,573 A | 9/1998 | Ljusberg-Wahren et al. | 424/450 |
| 5,858,398 A | 1/1999 | Cho | |
| 5,888,533 A | 3/1999 | Dunn | |
| 5,939,096 A | 8/1999 | Clerc et al. | 424/450 |
| 6,328,979 B1 | 12/2001 | Yamashita et al. | 424/400 |
| 6,482,517 B1 | 11/2002 | Anderson | 424/402.24 |
| 6,552,002 B2 | 4/2003 | Steber et al. | |
| 6,773,714 B2 | 8/2004 | Dun et al. | 424/426 |
| 7,662,408 B2 | 2/2010 | Saito et al. | 424/468 |
| 7,731,947 B2 | 6/2010 | Eliaz et al. | |
| 7,871,642 B2 | 1/2011 | Supersaxo et al. | |
| 9,173,853 B2 | 11/2015 | Lee et al. | 424/489 |
| 2003/0070679 A1 | 4/2003 | Hochrainer et al. | 128/203.15 |
| 2005/0112188 A1 | 5/2005 | Eliaz et al. | |
| 2005/0118206 A1 | 6/2005 | Luk et al. | 424/400 |
| 2006/0165766 A1 | 7/2006 | Barenholz et al. | 424/450 |

(Continued)

FOREIGN PATENT DOCUMENTS

| | | | |
|---|---|---|---|
| EP | 0 224 987 | | 6/1987 |
| JP | 2003-252748 | * | 9/2003 |

(Continued)

OTHER PUBLICATIONS

C. R. Scholfield. Composition of Soybean Lecithin. J American Oil Chemists' Society (JAOCS), Oct. 1981. pp. 889-892.*

(Continued)

*Primary Examiner* — Marcela M Cordero Garcia
(74) *Attorney, Agent, or Firm* — Dentons US LLP; Stephanie Seidman

(57) ABSTRACT

Disclosed is a sustained release lipid pre-concentrate, comprising: a) a sorbitan unsaturated fatty acid ester having a polar head with at least two or more —OH (hydroxyl) groups; b) a phospholipid; and c) a liquid crystal hardener, free of an ionizable group, having a hydrophobic moiety of 15 to 40 carbon atoms with a triacyl group or a carbon ring structure. The lipid pre-concentrate exists as a liquid phase in the absence of aqueous fluid and forms into a liquid crystal in the presence of aqueous fluid. Also, a pharmaceutical composition further comprising a pharmacologically active ingredient plus the pre-concentrate is provided.

17 Claims, 2 Drawing Sheets

(56) References Cited

U.S. PATENT DOCUMENTS

| | | | |
|---|---|---|---|
| 2006/0182790 A1* | 8/2006 | Mayoral | A61K 31/198 424/448 |
| 2007/0080323 A1 | 4/2007 | Joabsson et al. | 252/299.01 |
| 2008/0085263 A1 | 4/2008 | Thuresson et al. | 424/85.7 |
| 2008/0102128 A1 | 5/2008 | Constancis et al. | 424/489 |
| 2008/0274176 A1 | 11/2008 | Johnsson et al. | |
| 2009/0068255 A1* | 3/2009 | Yu et al. | 424/450 |
| 2010/0034801 A1 | 2/2010 | Li et al. | 424/94.61 |
| 2010/0048452 A1 | 2/2010 | Gaucheron et al. | |
| 2010/0129456 A1 | 5/2010 | Ishihara et al. | 424/489 |
| 2011/0091420 A1 | 4/2011 | Liu et al. | 424/85.4 |
| 2012/0177699 A1 | 7/2012 | Tong et al. | 424/400 |
| 2012/0269772 A1 | 10/2012 | Thuresson et al. | 424/85.7 |
| 2015/0110876 A1 | 4/2015 | Lee et al. | 424/489 |
| 2015/0265535 A1 | 9/2015 | Yu et al. | 424/400 |
| 2015/0290322 A1 | 10/2015 | Yoon et al. | 514/64 |
| 2015/0297726 A1 | 10/2015 | Yoon et al. | 514/10.3 |
| 2015/0322023 A1 | 11/2015 | Lee et al. | 546/290 |
| 2015/0374850 A1 | 12/2015 | Hwang et al. | 424/489 |
| 2016/0083354 A1 | 3/2016 | Lee et al. | 544/374 |

FOREIGN PATENT DOCUMENTS

| | | |
|---|---|---|
| JP | A 2007-511525 | 5/2007 |
| NZ | 280420 | 3/1997 |
| NZ | 280419 | 4/1997 |
| WO | WO 94/17830 | 8/1994 |
| WO | WO 98/47487 | 10/1998 |
| WO | WO 01/34111 | 5/2001 |
| WO | WO 2005/048930 | 6/2005 |
| WO | WO 2005/049069 | 6/2005 |
| WO | WO 2005/110360 | 11/2005 |
| WO | WO 2005/117830 | 12/2005 |
| WO | WO 2006/075124 | 7/2006 |
| WO | WO 2006/075125 | 7/2006 |
| WO | WO 2008/152401 | 12/2008 |
| WO | WO 2009/024795 | 2/2009 |
| WO | WO 2010/108934 | 9/2010 |
| WO | WO 2011/062420 | 5/2011 |
| WO | WO 2012/128417 | 9/2012 |
| WO | WO 2012/165468 | 12/2012 |

OTHER PUBLICATIONS

Tsuda et al. JP2003-252748 English machine translation. Sep. 2003. 5 pages.*
Rong, G. et al., "Complex Lamellar Structure of Polyoxyethylene 20 Sorbitan Oleate and a Fatty Acid/Lecithin Lamellar Liquid Crystal," Langmuir, 1996, 12:4286-4291.
Athanasiou, K. et al., "Sterilization, toxicity, biocompatibility and clinical applications of polylactic acid/polyglycolic acid copolymers," Biomaterials, 1996, 17:93-102.
Ljusberg-Wahren, H. et al., "Enzymatic characterization of lipid-based drug delivery systems," International Journal of Pharmaceutics, 2005, 298:328-332.
Sah, H. et al., "Effects of aqueous phase composition upon protein destabilization at water/organic solvent interface," Journal of Controlled Release, 2005, 106:51-61.
Letter/Written Disclosure of the Supplemental Information Disclosure Statement for the above-referenced application, mailed on Aug. 4, 2015, 2 pages.
International Search Report and Written Opinion, issued Dec. 12, 2012, in connection with International Patent Application No. PCT/KR2012/006855, 12 pages.
International Preliminary Report on Patentability, issued Mar. 4, 2014, in connection with International Patent Application No. PCT/KR2012/006855, 6 pages.
Australian Examination Report, issued on Mar. 24, 2015, in connection with Australian Patent Application No. 2012302422, 3 pages.
Supplementary European Search Report and Search Opinion, issued Apr. 28, 2015, in connection with European Patent Application No. EP 12 826 818, 2 pages.

U.S. Appl. No. 14/440,058, filed Dec. 27, 2013.
U.S. Appl. No. 14/440,059, filed Dec. 27, 2013.
U.S. Appl. No. 14/440,060, filed Dec. 27, 2013.
New Zealand Office Action dated Nov. 28, 2014 of New Zealand application No. 622165.
Letter/Written Disclosure of the Supplemental Information Disclosure Statement for the above-referenced application, mailed on Jan. 15, 2016, 2 pages.
English language transaltion of title and abstract of WO 2012/128417, published Sep. 27, 2012, 1 page.
Machine-generated English translation of WO 2012/128417, published Sep. 27, 2012, PatentScope, World Intellectual Property Organization, 6 pages.
Shah et al., "The ionic structure of lecithin monolayers." Journal of Lipid Research. 8:227-233 (1967).
Yeap et al., "Effect of calcium ions on the density of lecithin and its effective molecular volume in lecithin-water dispersions." Chemistry and Physics of Lipids. 151(1): 1-9 (2008).
International Search Report and Written Opinion, issued Apr. 9, 2014, in conncection with International Patent Application No. PCT/KR2013/012265, 12 pages.
International Search Report and Written Opinion, issued Apr. 28, 2014, in connection with International Patent Application No. PCT/KR2013/012269, 11 pages.
International Search Report and Written Opinion, issued Apr. 28, 2014, in conncection with International Patent Application No. PCT/KR2013/012259, 12 pages.
Examiner's Report, issued Feb. 12, 2015, in connection with Canadian Patent Application No. 2,845,784, 3 pages.
International Preliminary Report on Patentability, issued Jun. 30, 2015, in connection with International Patent Application No. PCT/KR2013/012269, 7 pages.
International Preliminary Report on Patentability, issued Jun. 30, 2015, in connection with International Patent Application No. PCT/KR2013/012259, 8 pages.
International Preliminary Report on Patentability, issued Jun. 30, 2015, in connection with International Patent Application No. PCT/KR2013/012265, 8 pages.
Response to Examiner's Report, submitted Jul. 28, 2015, in connection with Canadian Patent Application No. 2,845,784, 13 pages.
Official Action, issued Jul. 28, 2015, in connection with Japanese Patent Application No. 2014-528270, [Original document in Japanese and English translation], 5 pages.
Response, submitted Sep. 18, 2015, in connection with Australian Patent Application No. 2012302422, 18 pages.
Notice of Acceptance, issued Sep. 25, 2015, in connection with Australian Patent Application No. 2012302422, 2 pages.
Examiner's Report, issued Nov. 12, 2015, in connection with Canadian Patent Application No. 2,845,784, 4 pages.
Response to Supplementary European Search Report and Written Opinion, submitted Nov. 18, 2015, in connection with European Patent Application No. EP 12 826 818, 16 pages.
Letter/Written Disclosure of the Supplemental Information Disclosure Statement for the above-referenced application, filed herewith on Aug. 2, 2016, 2 pages.
Machine-generated English translation of WO 2012/165468, published Dec. 6, 2012, PatentScope, World Intellectual Property Organization, 16 pages.
Nema et al., "Excipients and their use in injectable products," PDA J Pharm Sci Technol 51(4):166-171 (1997).
Office Action, issued Feb. 15, 2016, in connection with Russian Patent Application No. 2014112189/15(019137) [English translation and original document in Russian], 8 pages.
Office Action, mailed Jul. 5, 2016, in connection with U.S. Appl. No. 14/440,059, 34 pages.
Examination Report, issued Jan. 13, 2016, in connection with Australian Patent No. 2013371098, 3 pages.
Extended European Search Report, issued May 17, 2016, in connection with European Patent Application No. 13868908.8, 7 pages.
Office Action, mailed May 31, 2016, in connection with Japanese Patent Application No. 550322/2015 [English language translation and original document in Japanese], 9 pages.

(56) References Cited

OTHER PUBLICATIONS

Examination Report, issued Sep. 23, 2015, in connection with New Zealand Patent Application No. 710471, 3 pages.
Response, filed Mar. 22, 2016, to Examination Report, issued Sep. 23, 2015, in connection with New Zealand Patent Application No. 710471, 11 pages.
Notification of Acceptance, dated Apr. 18, 2016, in connection with New Zealand Patent Application No. 710471, 1 page.
Examination Report, dated Jan. 13, 2016, in connection with Australian Patent Application No. 2013371101, 3 pages.
Office Action, dated Jun. 7, 2016, in connection with Japanese Patent Application No. 550323/2015 [English language translation and original document in Japanese], 14 pages.

* cited by examiner

Fig. 1
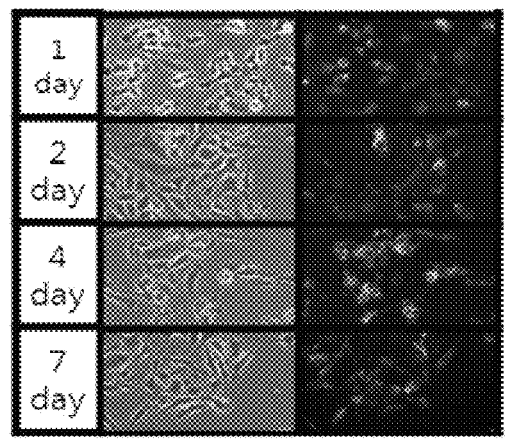
Fig. 2
Fig. 3
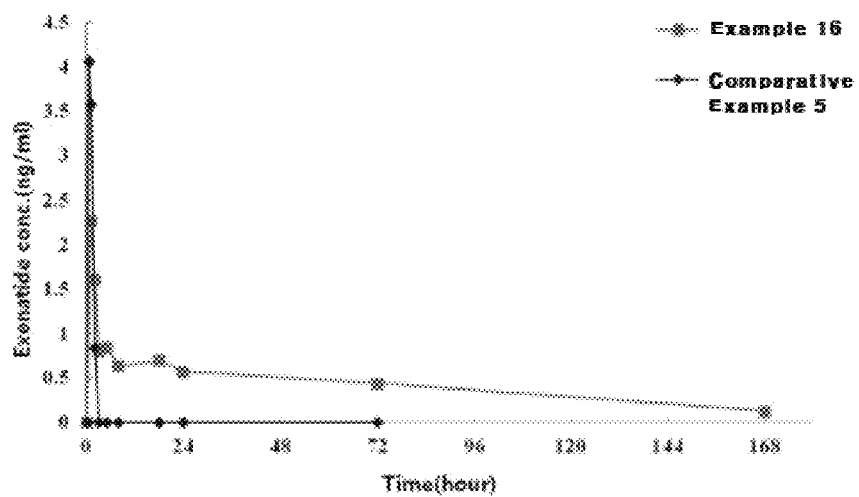

(Inj. = Injection)

SUSTAINED-RELEASE LIPID PRE-CONCENTRATE OF PHARMACOLOGICALLY ACTIVE SUBSTANCE AND PHARMACEUTICAL COMPOSITION COMPRISING THE SAME

CROSS-REFERENCE TO RELATED APPLICATIONS

This application is a national stage application of PCT/KR2012/006855, filed Aug. 28, 2012 and published as WO 2013/032207 on Mar. 7, 2013, which claims the benefit of Korean application no. 10-2011-0087160, filed Aug. 30, 2011, the entirety of each of which is incorporated herein by reference.

TECHNICAL FIELD

The present invention relates to a sustained release lipid pre-concentrate of a pharmacologically active substance and a pharmaceutical composition comprising the same.

BACKGROUND ART

Sustained release formulations are designed to release a single dose of a pharmacologically active substance at a predetermined rate in order to maintain the effective plasma concentration of the substance in blood stream for a specific period of time, with minimization of the side effects caused by multiple doses.

PLGA [poly(lactic-co-glycolic acid)] is a representative of the currently used biodegradable materials which are approved for use in sustained release by the Food and Drug Administration (FDA). U.S. Pat. No. 5,480,656 reported the sustained release of a pharmacologically active substance by way of the degradation of PLGA into lactic acid and glycolic acid over a specific period of time in vivo. However, the acidic degradation products of PLGA induce inflammation, decreasing cell growth (K. Athanasiou, G. G. Niederauer and C. M. Agrawal, Biomaterials, 17, 93 (1996)).

For the sustained release, PLGA solid particles of 10~100 micrometers in diameter, including a drug therein must be injected. The injection of the PLGA solid particles is accompanied by pain or inflammation, because the solid particle of 10~100 micrometers in diameter should be applied through sc or im injection and is degraded over a period of up to several months in injection site. There is therefore a need for a novel sustained release formulation that supplies the effective plasma concentration of a pharmacologically active substance for a prolonged period of time with improved patient compliance.

Culminating in the present invention, intensive and thorough research of the present inventors into the sustained release formulation led to the findings that a lipid pre-concentrate comprising a) a sorbitan unsaturated fatty acid ester having a polar head with at least two or more —OH (hydroxyl) groups; b) a phospholipid; and c) a liquid crystal hardener, free of an ionizable group, having a hydrophobic moiety of 15 to 40 carbon atoms with a triacyl group or a carbon ring structure, exists as a liquid state in the absence of aqueous fluid and transits into a gel-like liquid crystal upon exposure to aqueous fluid, showing an excellent sustained release profile, and that the pre-concentrate is safe to the body and highly biodegradable.

A description is given of the prior arts relevant to the present invention, infra.

International Patent Publication No. WO 2005/117830 describes a pre-formulation comprising a low viscosity, non-liquid crystalline, mixture of: at least one neutral diacyl lipid and/or at least one tocopherol, at least one phospholipid, and at least one biocompatible, oxygen-containing, low viscosity organic solvent. International Patent Publication No. WO 2006/075124 discloses pre-formulations of a low viscosity mixture containing at least one diacyl glycerol, at least one phosphatidyl choline, at least one oxygen-containing organic solvent, and at least one somatostatin analogue. All these pre-formulations release the pharmacologically active materials in vivo for two weeks or longer, but the use of a diacyl lipid, a component essential for the pre-formulations, as a pharmaceutical excipient is not usable and it has to be proven to be sufficiently safe. Another difference with the present invention is that the organic solvents used in the publications are found to decrease the activity of some drugs (H. Ljusberg-Wahre, F. S. Nielse, 298, 328-332 (2005); H. Sah, Y. bahl, Journal of Controlled Release 106, 51-61(2005)).

U.S. Pat. No. 7,731,947 discloses a composition comprising: a particle formulation comprising an interferon, sucrose, methionine, and a citrate buffer, and a suspending vehicle comprising a solvent such as benzyl benzoate, wherein the particle formulation is dispersed in the suspending vehicle. In one Example, it is described that phosphatidylcholine is dissolved together with vitamin E (tocopherol) in an organic solvent and is used to disperse the particle formulation therein. However, this composition is different from the transparent and filterable solution formulation of the present invention in that the composition is used to disperse solid particles and does not allow the formation of liquid crystals.

U.S. Pat. No. 7,871,642 discloses a method of preparing a dispersion for delivering a pharmacologically active agent, comprising dispersing a homogeneous mixture of a phospholipid, a polyoxyethylene coemulsifier, triglyceride and ethanol in water, wherein the polyoxyethylene coemulsifier is selected from among polyethoxylated sorbitan fatty acid esters (polysorbate) and polyethoxylated vitamin E derivatives. Polyethoxylated sorbitan fatty acid esters and polyethoxylated vitamin E derivatives, derived by conjugating the hydrophilic polymer polyoxyethylene to sorbitan fatty acid ester and vitamin E, respectively, are quite different in structure from sorbitan fatty acid ester and vitamin E. They are usually used as hydrophilic surfactants utilizing the property of polyoxyethylene, which is different from the component of the present invention.

U.S. Pat. No. 5,888,533 discloses a flowable composition for forming a solid biodegradable implant in situ within a body, comprising: a non-polymeric, water-insoluble, biodegradable material; and a biocompatible, organic solvent that at least partially solubilizes the non-polymeric, water-insoluble material and is miscible or dis-persible in water or body fluids, and capable of diffusing-out or leaching from the composition into body fluid upon placement within a body, whereupon the non-polymeric material coagulates or precipitates to form the solid implant. In this composition, sterols, cholesteryl esters, fatty acids, fatty acid glycerides, sucrose fatty acid esters, sorbitan fatty acid esters, fatty alcohols, esters of fatty alcohols with fatty acids, anhydrides of fatty acids, phospholipids, lanolin, lanolin alcohols, and mixtures thereof are described as the non-polymeric material, and ethanol is used as the solvent. However, differences from the present invention reside in that this composition cannot form liquid crystals and is designed to form solid implants by simple coagulation or precipitation of water-insoluble materials and that a lot of the organic solvent is necessarily used.

DISCLOSURE OF INVENTION

Technical Problem

It is therefore an object of the present invention to provide a lipid pre-concentrate based on a sorbitan unsaturated ester having a polar head with at least two —OH (hydroxyl) groups that has significantly high safety and biodegradability and exists a liquid state advantageous for injection applications of dosage form while forming into a liquid crystal upon exposure to aqueous fluid, thus enhancing the sustained release of a drug in vivo.

It is another object of the present invention to provide a lipid pre-concentrate which can be injected without producing pain or inflammations, problems with conventional formulations.

It is a further object of the present invention to provide a pharmaceutical composition further comprising a pharmacologically active ingredient plus the pre-concentrate of the present invention.

Solution to Problem

In accordance with an aspect thereof, the present invention provides lipid pre-concentrate for a sustained release, comprising a) a sorbitan unsaturated fatty acid ester having a polar head with at least two or more —OH (hydroxyl) groups; b) a phospholipid; and c) a liquid crystal hardener, free of an ionizable group, having a hydrophobic moiety of 15 to 40 carbon atoms with a triacyl group or a carbon ring structure, wherein said lipid pre-concentrate exists as a liquid phase in the absence of aqueous fluid and forms into a liquid crystal in the presence of aqueous fluid.

The sorbitan unsaturated fatty acid ester having a polar head with two or more —OH (hydroxyl) groups, useful in the present invention, is represented by the following Chemical Formula 1:

[Chemical Formula 1]

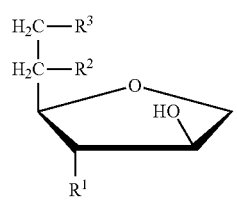

wherein R1 is OH, R2 is OH or R and R3 is R wherein R is an alkylester of 4 to 30 carbon atoms with one or more unsaturated bonds.

The sorbitan fatty acid ester, which accounts for the formation of a liquid crystal in the present invention, is different from conventional counterparts such as oleyl glycerate (OG), phytanyl glycerate (PG), and glycerine monooleate (GMO), glycerine dioleate (GDO, a kind of diacyl glycerol) of the following Chemical Formula 2. That is, the conventional molecules responsible for liquid crystalline phases share the common structure consisting of a polar head derived from glycerine or glyceric acid and a non-polar tail derived from a lipid alcohol or fatty acid.

[Chemical Formula 2]

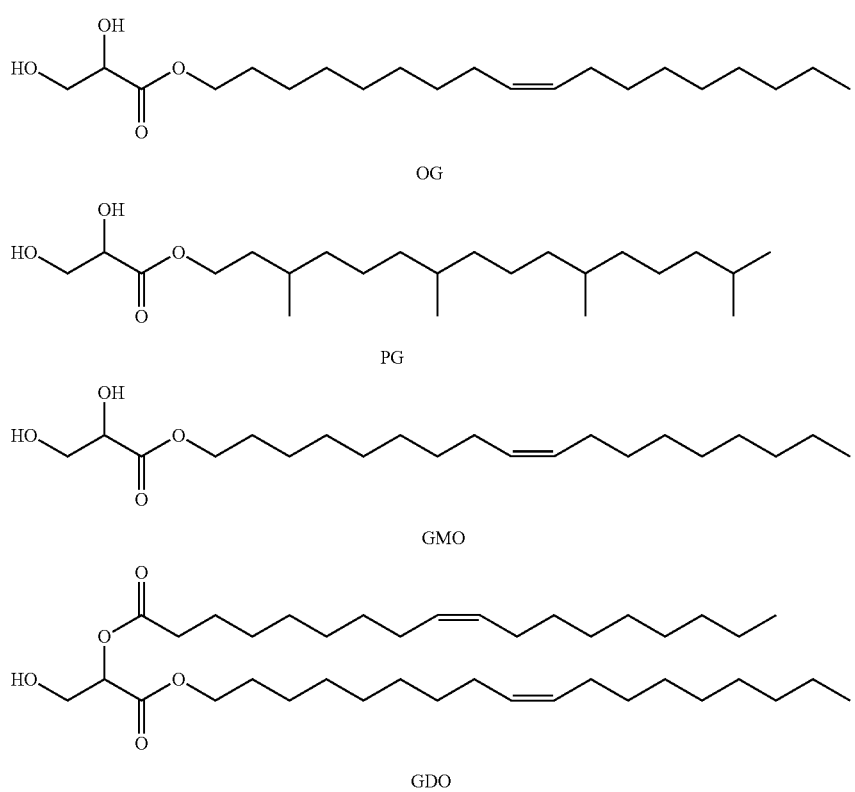

However, the conventional molecules responsible for liquid crystalline phases are somewhat difficult to apply to the development of medications because of the following disadvantages. Oleyl glycerate (OG) and phytanyl glycerate (PG), although capable of readily form into liquid crystals, are rarely used as pharmaceutical excipients for human medicine because of their relatively high toxicity. On the other hand, glycerine monooleate is useful as a pharmaceutically acceptable excipient, but has weak crystallinity to form liquid crystals necessary for sustained release medications.

Glycerol dioleate, which is used in International Patent Publication No. WO 2005/117830 as described supra, is a diacyl lipid with glycerin functioning as a polar head. This molecule is not generally used as a pharmaceutical excipient because its safety has not yet been proven. In addition, it is significantly poor in biodegradability.

As a result of intensive and thorough research, the present inventors found that sorbitan unsaturated fatty acid esters have advantages over conventionally used liquid crystalline molecules, glycerine or glyceric acid derivatives in that they form liquid crystals very effective for the sustained release of active ingredients, with superiority in safety and biodegradability and are applicable to the development of medical products overcoming the problems encountered in the prior art. For use in compositions for medicaments, materials must be guaranteed to be safe and biodegradable. Further, biodegradability is a very important factor for the material which is in charge of sustained release in the body. If the sustained release injection using PLGA is designed to release an active ingredient for one week, it is ideal that the PLGA is degraded in vivo one week after injection. In fact, however, PLGA remains intact for one to several months even after the function of sustained release is finished. Therefore, the sorbitan unsaturated fatty acid ester of the present invention, which has excellent sustained release property, safety and biodegradability, is applicable for a novel liquid crystal-inducing material with great value in pharmaceutical industry.

The fatty acid of sorbitan unsaturated fatty acid ester of the present invention may be derived from vegetable oil (e. g., palm oil, castor oil, olive oil, peanut oil, sweet oil, corn oil, sesame oil, cottonseed oil, soybean oil, sunflower oil, safflower oil, linseed oil), animal fat and oil (e. g., milk fat, lard, tallow, etc.), whale oil and fish oil. Sorbitan unsaturated fatty acid ester of the present invention may be selected from among sorbitan monoesters, sorbitan sesquiesters, sorbitan diesters and mixtures thereof. Sorbitan monoester is a sorbitan molecule with one fatty acid group attached thereto via an ester bond and may be selected from among sorbitan monooleate, sorbitan monolinoleate, sorbitan monopalmitoleate, sorbitan monomyristoleate and a mixture thereof. Sorbitan sesquiester is a sorbitan molecule to which 1.5 fatty acid groups are attached on average via an ester bond. Representative among the sorbitan sesquiester useful in the present invention are sorbitan sesquioleate, sorbitan sesquilinoleate, sorbitan sesquipalmitoleate, sorbitan sesquimyristoleate and a mixture thereof. Sorbitan diester is a sorbitan molecule with two fatty acid groups attached thereto via an ester bond, and may be selected from sorbitan dioleate, sorbitan dilinoleate, sorbitan dipalmitoleate, sorbitan dimyristoleate and a mixture thereof.

Phospholipids are essential for the construction of lamellar structures such as liposomes, but cannot form a non-lamellar phase structure, such as a liquid crystal, by themselves. However, phospholipids can participate in the sorbitan unsaturated fatty acid ester-driven formation of non-lamellar phase structures, serving to stabilize the resulting liquid crystals. The phospholipid useful in the present invention contains a saturated or unsaturated alkyl ester group of 4 to 30 carbon atoms with a polar head. The phospholipid may be selected from among phosphatidylcholine, phosphatidylethanolamine, phosphatidylserine, phosphatidylglycerine, phosphatidylinositol, phosphatidic acid, sphingomyelin, and a mixture thereof. Phospholipids are found in plants and animals such as soybean and eggs. In phospholipids, long fatty acid hydrocarbon chains which account for the hydrophobic tails include saturated fatty acid chains such as mono- and dipalmitoyl, mono- and dimyristoyl, mono- and dilauryl, and mono- and distearyl, unsaturated fatty acid chains such as mono- or dilinoleyl, mono- and dioleyl, mono- and dipalmitoleyl, mono- and dimyristoleyl, and a mixture thereof.

The liquid crystal hardener cannot form a non-lamellar structure (liquid crystal) unlike sorbitan unsaturated fatty acid esters, nor a lamellar structure (liposome) unlike phospholipids, by itself. However, the liquid crystal hardener contributes to the sorbitan unsaturated fatty acid ester-driven formation of non-lamellar phase structures by increasing the curvature of the non-lamellar structures to enhance the ordered co-existence of oil and water in nano-scale. In the interests of this function, the liquid crystal hardener is required to have a highly limited polar moiety and a bulky non-polar moiety within the inside of its molecular structure.

In practice, biocompatible molecules which are injectable into the body can be selected as the liquid crystal hardener of the present invention only via experimental 'trial and error'. As a result, liquid crystal hardeners suitable for the composition of the present invention have molecular structures which are different from one another and thus cannot be elucidated as one molecular structure. The common structural feature deduced from all of the selected liquid crystal hardeners is that they are free of ionizable groups, such as carboxyl and amine groups, and have hydrophobic moieties of 15 to 40 carbon atoms comprising a bulky carbon ring structure or a triacyl group. Preferred examples of the liquid crystal hardener of the present invention may be free of ionizable groups, such as carboxyl and amine groups, and having with at most one ester and —OH (hydroxyl) group as a polar head, and having hydrophobic moieties of 20 to 40 carbon atoms comprising a bulky carbon ring structure or a triacyl group. Preferred examples of the liquid crystal hardener of the present invention may include, but are not limited to, triglyceride, retinyl palmitate, tocopheryl acetate, cholesterol, benzyl benzoate and a mixture.

In the composition of the present invention, the weight ratio between components of a) and b) is in a range of from 10:1 to 1:10 and preferably in a range of 5:1 to 1:5. The weight ratio of a)+b) to c) falls within the range of from 100:1 to 1:1 and preferably within the range of from 50:1 to 2:1. Forming desired liquid crystals, the components in such weight ratios guarantee effective sustained release.

As used herein, the term "aqueous fluid" is intended to include water and body fluid such as a mucosal solution, a tear, sweat, saliva, gastrointestinal fluid, extravascular fluid, extracellular fluid, interstitial fluid, and plasma. When brought into contact with body surfaces, regions or cavities (e.g. inside the body) whose external environments are accounted for by aqueous fluids, the composition of the present invention undergoes transition from a sol-like liquid phase to a gel-like liquid crystalline phase. That is, the composition of the present invention is a pre-concentrate which exists as a liquid state before application to the human body and shifts into a liquid crystalline phase promising sustained release within the body.

The liquid crystals formed by the composition of the present invention have a non-lamellar phase structure in which oil and water are in ordered mixture and arrangement without discrimination between inner and out phases. The ordered arrangement of oil and water renders the non-lamellar phase structure of a mesophase, which is a state of matter intermediate between liquid and solid. The pre-concentrate of the present invention is different from conventional compositions that form lamellar structures, such as micelles, emulsions, microemulsions, liposomes, and lipid bilayers, which have been widely used in designing pharmaceutical formulations. Such lamellar structures are in oil in water (o/w) or water in oil (w/o) type in which there is clear discrimination inner and out phases.

The term "liquid crystallization," as used herein, refers to the formation of liquid crystals having a non-lamellar phase structure from the pre-concentrate upon exposure to aqueous fluid.

The lipid pre-concentrate of the present invention may be prepared at room temperature from a composition comprising at least one sorbitan unsaturated fatty acid ester having a polar head with at least two or more —OH (hydroxyl) groups, at least one phospholipid, and at least one liquid crystal hardener, if necessary, by heating or using a homogenizer.

The homogenizer may be a high-pressure homogenizer, an ultrasonic homogenizer, a bead mill homogenizer, etc.

As described above, because the lipid pre-concentrate of the present invention may be a pharmaceutical composition which exists as a liquid phase in the absence of aqueous fluid and forms into liquid crystals in the presence of aqueous fluid in the body, it can be administered using a method selected from among injection, coating, dropping, padding, oral administration, and spraying. And the pre-concentrate of the present invention may be formulated into various dosage forms including injections, ointments, gels, lotions, capsules, tablets, liquids, suspensions, sprays, inhalers, eye drops, adhesives, and patches.

Particularly, when an injection route is taken, the pre-concentrate of the present invention may be administered by subcutaneous or intramuscular injection or other injection routes depending on the properties of the pharmacologically active ingredient used.

The pharmacologically active ingredient applicable to the pre-concentrate of the present invention may be selected from among a protein, a peptide, a vaccine, a gene, a non-peptidic hormone, a synthetic chemical, and a combination thereof.

Examples of the protein or peptide as a pharmacologically active ingredient in the composition of the present invention include erythropoietin, growth hormones (human, pig, cow, etc.), growth hormone releasing factors, nerve growth factors, G-CSF, GM-CSF, M-CSF, blood coagulation factors, insulin, oxytocin, vasopressin, adrenocorticotropic hormone, epidermal growth factor, platelet-derived growth factor, prolactin, somatostatin, glucagon, interleukin-2 (IL-2), interleukin-11 (IL-11), gastrin, tetragastrin, pentagastrin, urogastron, secretin, calcitonin, enkephalin, endorphin, angiotensin, thyroid stimulating hormone-releasing hormone, tumor necrosis factor, tumor necrosis factor-related apoptosis inducing ligand, heparinase, bone morphogenic protein, hANP, glucagon-like peptide, rennin, bradykinin, bacitracin, polymyxin, colistin, tyrocidin, gramicidin, cyclosporine, polyethylene glycol-conjugated proteins and their synthetic analogs, monoclonal antibodies, enzymes, cytokines and a combination, but not limited thereto.

The non-peptidic hormones are a class of hormones which are not proteins or peptides and may be selected from among, but not limited to, testosterone, estradiol, progesterone, prostaglandin, finateride, dutasteride, synthetic analogs thereof, and combinations thereof.

Examples of the gene entrapped within the pre-concentrate of the present invention include plasmid DNA, siRNA, polynucleotides, oligodeoxynucleotides, anti-sense oligonucleotides, and a mixture thereof, but are not limited thereto.

The synthetic chemical may be selected from among tacrolimus, anatrozole, olanzapine, aripiprazole, risperidone, medroxyprogesterone, naltrexone, methotrexate, pinitol, olopatadine, latanoprost, anecortave, triptorelin pamoate, minoxidil, tibolone, solifenacin, tadalafil, varenicline, ropinirole, fentanyl, ketotifen, montelukast and a combination thereof, but are not limited thereto.

Accordingly, in accordance with another aspect thereof, the present invention provides a pharmaceutical composition comprising d) a pharmacologically active ingredient selected from among proteins, peptides, vaccines, genes, non-peptidic hormones, synthetic chemicals, and a combination thereof, in addition to the lipid pre-concentrate of the present invention.

Descriptions about the ingredients a) to c) and the liquid crystal used in the pharmaceutical composition may refer to those given with regards to the lipid pre-concentrate.

In addition, the description of the pharmacologically active ingredient d) of the pharmaceutical composition may be the same as that given with respect to the lipid pre-concentrate.

The pharmaceutical composition may preferably be formulated as an injection, an ointment, a gel, a lotion, a capsule, a tablet, a liquid, a suspension, a spray, an inhaler, an eye drop, an adhesive, and a patch, but not limited thereto. More preferably, it may be formulated as an injection.

The content of the pharmacologically active ingredient in the pharmaceutical composition of the present invention varies depending on the kind thereof and the formulation to be used, and is generally within the range of from 0.0001 to 90 weight % based on the total weight of the pharmaceutical composition.

The pharmaceutical composition of the present invention may be prepared by adding a pharmacologically active ingredient to the pre-concentrate of the present invention. If necessary, heat or a homogenizer may be used in the preparation of the pharmaceutical composition of the present invention, but this is not a limiting factor to the present invention.

The dose of the pharmaceutical composition of the present invention adheres to the well-known dose of the pharmacologically active ingredient employed and may vary depending on various factors including the patient's condition, age and sex. It may be administered orally or parenterally.

In accordance with a further aspect thereof, the present invention contemplates a method of maintaining pharmaceutical efficacy through the sustained release of a pharmacologically active ingredient by administering the pharmaceutical composition of the present invention to a mammal including a human, and the use of the pharmaceutical composition for the sustained release of a pharmacologically active ingredient.

Advantageous Effects of Invention

As described hitherto, the lipid pre-concentrate of the present invention, based on a sorbitan unsaturated fatty acid ester, is highly safe and biodegradable and exists as a liquid phase in the absence of aqueous fluid but rapidly changes into liquid crystals upon exposure to aqueous fluid within the body. When formulated with a pharmacologically active ingredient, therefore, the pre-concentrate in a liquid phase improves patient compliance and exhibits excellent sustained release without side effects such as pain and inflammation, compared to conventional sustained release formulations in solid particle phases.

BRIEF DESCRIPTION OF DRAWINGS

The above and other objects, features and other advantages of the present invention will be more clearly understood from the following detailed description taken in conjunction with the accompanying drawings, in which:

FIG. 1 shows in vivo biodegradability of the compositions of Examples 4 and 5 and Comparative Examples 1 to 3.

FIG. 2 shows in vitro drug release behaviors of the composition of Example 14;

FIG. 3 is a pharmacokinetic profile showing the in vivo drug release behavior of the compositions of Example 16 and Comparative Example 5;

MODE FOR THE INVENTION

Figure 4:
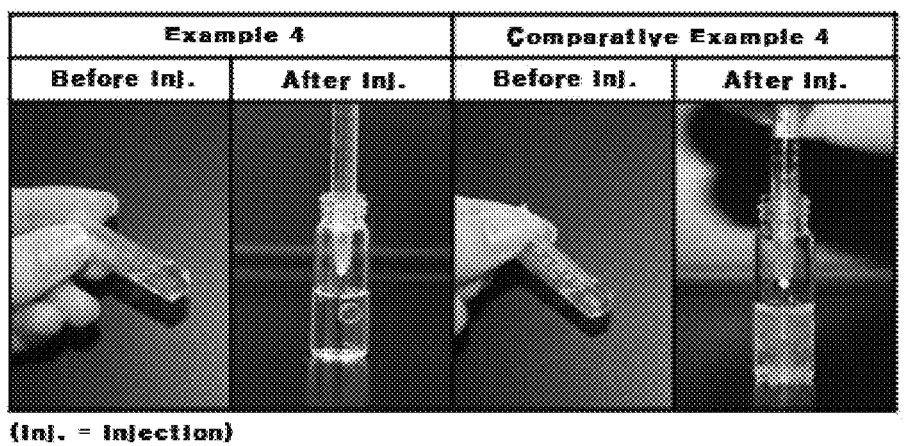
FIG. 4 shows phase changes of the compositions of Examples 4 and Comparative Example 4 upon exposure to aqueous fluid.

The following non-limiting Examples serve to illustrate selected embodiments of the invention. It will be appreciated that variations in proportions and alternatives in elements of the components shown will be apparent to those skilled in the art and are within the scope of embodiments of the present invention.

The additives and excipients used in the present invention satisfied the requirements of the Korean Pharmacopoeia and were purchased from Aldrich, Lipoid, and Croda.

Examples 1 to 11

Preparation of Lipid Pre-Concentrates

Sorbitan unsaturated fatty acid esters having a polar head with at least two —OH groups, phospholipids and liquid crystal hardeners were mixed at the weight ratios shown in Table 1 below, optionally in a solvent. In Examples 1 to 4, the ingredients were mixed in a water bath maintained at 25~45° C. using a homogenizer (PowerGen model125. Fisher) for about 10 min at 3,000 rpm. The ingredients of Examples 5 and 6 were stirred for 3 hours in a water bath maintained at 30~50° C. In Examples 7 to 11, the ingredients were mixed in a water bath maintained at 45~75° C. using a homogenizer (PowerGen model125. Fisher) for about 20 min at 3,000 rpm. Thereafter, the resulting lipid solutions were left at room temperature to make a thermal equilibrium at 25° C. before being loaded into 1 cc disposable syringes. Lipid pre-concentrates afforded by the above method are injected into water (2 g of distilled water) and formed into a liquid crystal phase.

TABLE 1

| Ingredient | Example No. (Unit: mg) | | | | | | | | | | |
|---|---|---|---|---|---|---|---|---|---|---|---|
| | 1 | 2 | 3 | 4 | 5 | 6 | 7 | 8 | 9 | 10 | 11 |
| Sorbitan monooleate | 40 | 50 | 60 | 60 | 40 | 65 | | | | | |
| Sorbitan sesquioleate | | | | | | | 40 | 50 | 60 | 60 | 65 |
| Phosphatidylcholine | 55 | | | 35 | 48 | | 55 | | | 30 | |
| Phosphatidylethanolamine | | 42.5 | | | | 25 | | 42.5 | | | 25 |
| Phosphatidylserine | | | 32.5 | | | | | | 32.5 | | |
| Triglyceride | 5 | 7.5 | | | | | 5 | 7.5 | | | |
| Retinyl palmitate | | | 7.5 | | | | | | 7.5 | | |
| Tocopheryl acetate | | | | 5 | | | | | | 10 | |
| Benzyl benzoate | | | | | 7 | | | | | | |
| Cholesterol | | | | | | 5 | | | | | 5 |
| Ethanol | | | | | 5 | 5 | | | | | 5 |
| Form in water phase | LC* | LC* | LC* | LC* | LC* | LC* | LC* | LC* | LC* | LC* | LC* |

*LC: liquid crystal

Examples 12 to 21

Preparation of Pharmaceutical Compositions Containing Pharmacologically Active Ingredients Sorbitan unsaturated fatty acid esters having a polar head with at least two —OH groups, phospholipids and liquid crystal hardeners were mixed at the weight ratios shown in Table 2 below.

In Examples 12 to 15, the ingredients were mixed in a water bath maintained at 30~60° C. using a homogenizer (PowerGen model125. Fisher) for about 10 min at 3,000 rpm. In Examples 16 to 21, the ingredients were mixed in a water bath maintained at 25~50° C. using a homogenizer (PowerGen model125. Fisher) for about 5 min at 3,000 rpm. The resulting lipid solutions were left at room temperature to make a thermal equilibrium at 25° C., followed by adding pharmacologically active ingredients thereto. As the pharmacologically active ingredients, the gene drugs siRNA (Bioneer) and fluorescence-conjugated siRNA (Invitrogen, Block-iT Fluorescent oligo), the peptide drug exenatide (Teva), and the synthetic drug tamsulosin (Lekpharmaceuticals) were used. Subsequently, the ingredients were homogenized using a homogenizer at 3,000 rpm for about 5 min to afford a pharmaceutical composition in a solution phase. In the case of the gene drugs (siRNA, fluorescence-conjugated siRNA), they were mixed in the amounts shown in Table 2, together with a solution of chitosan in distilled water, to form complexes before application to the lipid solutions.

TABLE 2

| Ingredient | Example No. (Unit: mg) | | | | | |
|---|---|---|---|---|---|---|
| | 12 | 13 | 14 | 15 | 16 | 17 |
| siRNA/Chitosan | 0.02/0.4 | 0.02/0.4 | | | | |
| Fluorescence-Conjugated siRNA/Chitosan | | | 0.02/0.4 | 0.02/0.4 | | |
| Exenatide | | | | | 0.13 | 0.13 |
| Sorbitan monooleate | 49 | | 49 | | 44 | |
| Sorbitan sesquioleate | | 59 | | 59 | | 54 |
| Phosphatidylcholine | 46 | | 46 | | 46 | |
| Phosphatidylethanolamine | | 36 | | 36 | | 36 |
| Tocopheryl acetate | 5 | | 5 | | 10 | |
| Benzyl benzoate | | 5 | | 5 | | 10 |

| Ingredient | Example No. (unit: mg) | | | |
|---|---|---|---|---|
| | 18 | 19 | 20 | 21 |
| Dutasteride | 0.5 | 0.5 | | |
| Tamsulosin | | | 0.2 | 0.2 |
| Sorbitan monooleate | 49 | | 45 | |
| Sorbitan sesquioleate | | 59 | | 35 |
| Phosphatidylcholine | 46 | | 40 | |
| Phosphatidylethanolamine | | 36 | | 50 |
| Tocopheryl acetate | 5 | | 15 | |
| Retinyl palmitate | | 5 | | 15 |

Comparative Examples 1 to 4

In Comparative Examples 1 to 3, dioleyl glyceride, a class of diacyl glycerides, was used in the amounts shown in Table 3, together with phosphatidylcholine, tocopherol and/or ethanol, followed by homogenization for about 10 min at 3,000 rpm in a homogenizer (PowerGen model125. Fisher).

In Comparative Example 4, polyoxyethylene sorbitan monooleate, phosphatidylcholine and tocopheryl acetate were used in the amounts shown in Table 3, followed by homogenization for about 30 min for 3,000 rpm in a homogenizer. Here, polyoxyethylene sorbitan monooleate has a polyoxyethylene group substituted for an —OH group on the sorbitan polar head and is different from sorbitan monooleate, used in the present invention. Polyoxyethylene sorbitan monooleate is generally used as a hydrophilic surfactant or emulsifier due to the bulky polyoxyethylene moiety.

TABLE 3

| Ingredient | Comparative Example No. (unit: mg) | | | |
|---|---|---|---|---|
| | 1 | 2 | 3 | 4 |
| Glyceryl dioleate | 65 | 55 | 52.5 | — |
| Polyoxyethylene sorbitan monooleate | — | — | — | 60 |
| Tocopherol | — | — | 7.5 | — |
| Tocopheryl acetate | — | — | — | 10 |
| Phosphatidylcholine | 35 | 35 | 30 | 30 |
| Ethanol | — | 10 | 10 | — |

Comparative Example 5

To 1 mL of physiological saline was added 20 μg of exenatide, followed by homogenization at room temperature.

Experimental Example 1

Comparison of In Vitro Safety

The safety of the compositions of the present invention was examined in vitro by executing an extraction colony assay cytotoxicity test as follows. In 18 mL of Eagle's Minimal Essential Media (EMEM) supplemented with 10% fetal bovine serum, 2 g of each of the compositions of Examples 1, 4 and Comparative Examples 1 and 2 was extracted. L929 cells (mouse fibroblast, American Type Culture Collection) were seeded at a density of $1\times10^2$ cells/well into 6-well plates and incubated for 24 hours at 37° C. in 5% $CO_2$ humidified incubator. The extracts were diluted in EMEM (0, 5, 25, 50%) and then placed in an amount of 2 mL/well in contact with the stabilized L929 cells. After incubation for 7 days at 37° C. in a 5% $CO_2$ humidified incubator, the cells were fixed with a 10% formalin solution and stained with a Giemsa solution to count colonies. The results are summarized in Table 4, below.

TABLE 4

| Extract Medium(v/v)%** | Relative colony formation rates(%)* | | | |
|---|---|---|---|---|
| | Ex. 1 | Ex. 4 | C. Ex. 1 | C. Ex. 2 |
| 0% Medium (control) | 100.0 | 100.0 | 100.0 | 100.0 |
| 5% Medium | 100.0 | 96.6 | 71.4 | 72.2 |
| 25% Medium | 66.7 | 72.4 | 23.8 | 27.8 |
| 50% Medium | 11.1 | 17.2 | 0.0 | 0.0 |

*Relative colony formation rates (%) = No. of Colonies on Test Medium/No. of Colonies on 0% Medium x 100 (%)
**Extract Medium % = Extract Medium/(Diluted Medium + Extract Medium) x 100(%)

As can be seen in Table 4, the groups administered with the compositions of Examples 1 and 4 showed significantly high cell growth rates on all diluted mediums (5%, 25% and 50%), compared to those administered with the compositions of Comparative Examples 1 and 2, indicating that the compositions (lipid pre-concentrates) of the present invention are far safer than the conventional compositions (disclosed in International Patent Publication No. WO 2005/117830).

Experimental Example 2

Comparison of In Vivo Biodegradability

The compositions of the present invention were evaluated for in vivo biodegradability in the following experiments.

Each of the compositions of Examples 4 and 5 was subcutaneously injected at a dose of 400 mg into the back of SD rats and monitored for a predetermined period of time. For comparison, the compositions of Comparative Examples 1 to 3 were tested in the same manner. The injection sites were photographed two weeks after injection and are shown in FIG. 1.

As can be seen in FIG. 1, the compositions of Examples 4 and 5 were observed to be mostly biodegraded almost without producing a feeling of irritation whereas the compositions of Comparative Examples 1 to 3 remained one to two third their original volume.

Therefore, the compositions of Examples 4 and 5 exhibited significantly high biodegradability, compared to the compositions of Comparative Examples 1 to 3 (International Patent Publication No. WO 2005/117830).

For reference, the conventional material PLGA [poly(lactic-co-glycolic acid)], which has been widely used for sustained release, is known to remain undegraded in vivo even after two or three months.

Accordingly, the lipid pre-concentrates of the present invention overcome the problem that even after it releases drugs completely, the conventional carrier system remains within the body due to its low biodegradability.

Experimental Example 3

In Vitro Test for Sustained Release

Drug release behaviors from the compositions of the present invention were examined in vitro in the following test. Prostate cancer cells (Prostate cancer-3, the Korean Cell Line Bank) were seeded at a density of 5×104 cells/well into transwell plates and incubated for 2 days at 37° C. in a 5% $CO_2$ humidified incubator. The composition of Example 14 was added in an amount of 100 mg to a transwell insert containing 3 mL of RPMI 1640 supplemented with 10% fetal bovine serum. Fluorescence emitted from the composition of Example 14 was measured using a fluorescence microscope (Eclipse Ti-S, Nikon) while the insert was applied every 24 hours for seven days to the transwell plates. The results are shown in FIG. 2.

The left photographs of FIG. 2 were taken using differential interference contrast (DIC) microscopy while the right photographs show the intracellular uptake of fluorescence-conjugated siRNA. As is understood from the data of FIG. 2, the composition of the present invention constantly released the pharmacologically active ingredient for at least 7 days.

Experimental Example 4

In Vivo Test for Sustained Release

Drug release behaviors from the compositions of the present invention were examined in vivo in the following test. The composition of Example 16 was subcutaneously injected into 6 SD rats (male), 9 weeks old, with an average body weight of 300 g, at such a dose as to correspond to 140 µg/kg of exenatide.

Exenatide concentrations in plasma samples taken from the SD rats were monitored for 14 days using a commercially available kit (immunoassay kit, Bachem) to draw a PK profile (pharmacokinetic profile) as shown in FIG. 3. For comparison, the composition of Comparative Example 5 was administered at a dose corresponding to 10 µg/kg of exenatide (herein, the reason why the dose of exenatide of Example 16 was 14 times as large as that of Comparative Example 5, is that the one-week dose (7 days) of the sustained release formulation corresponds to 14 times as large a dose as the general injection because of the use of twice a day).

As shown in FIG. 3, the composition of Example 16 increased the in vivo half-life of the biologically active ingredient by about 25 fold, compared to the composition of Comparative Example 1, which is a general injection, proving its excellent sustained release effect (in FIG. 3, means of measurements taken of 6 rats are plotted).

Experimental Example 5

In Vivo Test for Pharmacological Effect

The pharmacological effect of the composition of the present invention was evaluated in the following test. The composition of Example 16 containing exenatide (anti-diabetic), which can induce a weight loss, was subcutaneously injected into 6 SD rats (male), 9 weeks old, with an average body weight of 300 g, at such a dose as to correspond to 140 µg/kg of exenatide. Average weights were calculated on day 0 and 14 and the results are given in Table 5, below.

TABLE 5

|  | Example 16 (g) | Physiological Saline (g) |
|---|---|---|
| Day 0 | 303 | 308 |
| Day 14 | 356 | 379 |
| Wt Change(%)* | 75 | 100 |

(*Weight Change (%) = weight change of group administered with the composition of Example 16 (g)/weight change of group administered with physiological saline (g) × 100)

As shown in Table 5, the group administered with the composition of Example 16 experienced about 25% weight loss for two weeks, compared to the weight of the group administered with physiological saline. Therefore, the sustained release composition of the present invention ensures long-lasting pharmacological efficacy in vivo as well as significantly increased half-life of the biologically active ingredient through in vivo test for sustained release (EXPERIMENTAL EXAMPLE 4).

Experimental Example 6

Formation of Liquid Crystal in Aqueous Fluid

The composition of the present invention was evaluated for ability to form liquid crystal in an aqueous phase in the following test. After being loaded into syringes, compositions of Example 4 and Comparative Example 4 were dropped into 2 g of PBS (pH 7.4) and the results are shown in FIG. 4.

The composition of Example 4 based on the sorbitan unsaturated fatty acid ester having a polar head with at least two —OH (hydroxyl) groups (sorbitan monooleate) existed as a liquid phase in the absence of aqueous fluid, but formed liquid crystals upon exposure to aqueous fluid. On the other hand, the composition of Comparative Example 4 based on polyoxyethylene sorbitan unsaturated fatty acid ester (polyoxyethylene sorbitan monooleate) existed as a liquid phase and dispersed in PBS, but did not forms into a liquid crystal even after exposure to aqueous fluid. Consequently, only the composition of the present invention rapidly forms into liquid crystals contributing to sustained release effect in the presence of aqueous fluid, such as in the environment within the body.

Within the liquid crystals, there are a great number of bicontinuous water channels of nano size (below 20 nm) that resemble the Moebius strip. The water channels are surrounded with bicontinuous lipid layers. Thus, once a lipid composition forms into a liquid crystal in a semi-solid phase, a pharmacologically active substance can be released from the liquid crystal structure only after it has passed through numerous water channels and lipid layers, which enhances sustained release effect of a pharmacologically active substance. Therefore, the composition of the present invention can be applied to sustained release drug formulations.

Experimental Example 7

Determination of Inner Structure of Liquid Crystal Using Cryo TEM

Inner Structure of the liquid crystals of the composition of the present invention were examined in the following experiment. The composition of Example 4 in a liquid phase was dropped to 2 g of water to produce a liquid crystalline structure. Using a homogenizer, the liquid crystals in the aqueous phase were sufficiently dispersed and maintained in an equilibrium state at room temperature until analysis. The diluted liquid crystals were adsorbed onto a grid and frozen, followed by examining the structure in a cryo Transmission Electron Microscope (Cryo TecaiF20G2, FEI). The results are shown in FIG. 5.

Figure 5:
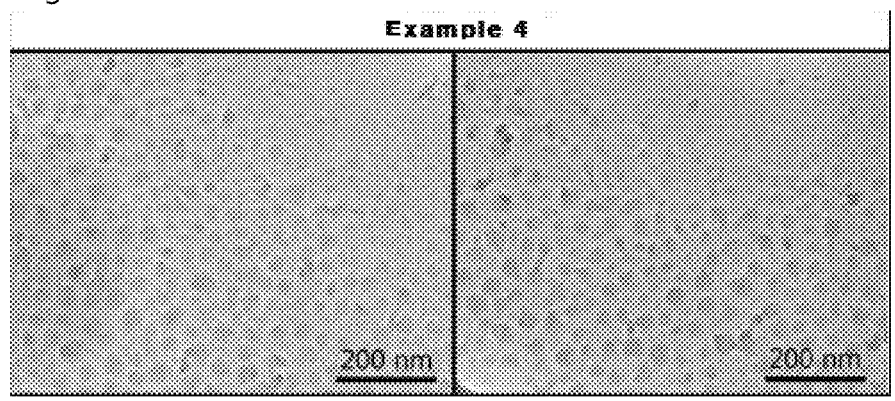
FIG. 5 shows the liquid crystalline structures of the composition of Example 4 in Cryo TEM microphotographs.

As shown in photographs of FIG. 5, the liquid crystals were observed to have crystalline structures such as cubic phases or hexagonal phases. As a rule, lamellar structures, such as micelles, emulsions, microemulsions, liposomes, etc., typically exist in complete spherical states, whereas non-lamellar structures according to the composition of the present invention assume ordered forms with certain angles, which are quite different from sphere forms.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The invention claimed is:

1. A sustained release lipid pre-concentrate, comprising:
a) a sorbitan unsaturated fatty acid ester having two or more —OH (hydroxyl) groups on a polar head and having the structure of Formula 1:

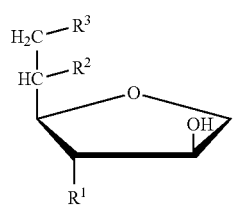

Formula 1 wherein:
$R^1$ is OH;
$R^2$ is OH or an alkylester of 4 to 30 carbon atoms with one or more unsaturated bonds; and
$R^3$ is an alkylester of 4 to 30 carbon atoms with one or more unsaturated bonds;
b) a phospholipid; and
a liquid crystal hardener selected from the group consisting of triglyceride having a hydrophobic moeity of 15 to 40 carbon atoms, tocopheryl acetate, cholesterol, benzyl benzoate and a mixture thereof
wherein the lipid pre-concentrate exists in a liquid state in the absence of an aqueous fluid and transforms from the liquid state into a liquid crystal gel state in the presence of an aqueous fluid.

2. The sustained release lipid pre-concentrate of claim 1, wherein the sorbitan unsaturated fatty acid ester is selected from the group consisting of sorbitan monooleate, sorbitan monolinoleate, sorbitan monopalmitoleate, sorbitan monomyristoleate, sorbitan sesquioleate, sorbitan sesquilinoleate, sorbitan sesquipalmitoleate, sorbitan sesquimyristoleate, sorbitan dioleate, sorbitan dilinoleate, sorbitan dipalmitoleate, sorbitan dimyristoleate and a mixture thereof.

3. The sustained release lipid pre-concentrate of claim 1, wherein the sorbitan unsaturated fatty acid ester is selected from the group consisting of sorbitan monooleate, sorbitan monolinoleate, sorbitan monopalmitoleate, sorbitan monomyristoleate and a mixture thereof.

4. The sustained release lipid pre-concentrate of claim 1, wherein the phospholipid contains a saturated or unsaturated alkyl ester group of 4 to 30 carbon atoms and is selected from the group consisting of phosphatidylcholine, phosphatidylethanolamine, phosphatidylserine, phosphatidylglycerine, phosphatidylinositol, phosphatidic acid, sphingomyelin and a mixture thereof.

5. The sustained release lipid pre-concentrate of claim 1, wherein the liquid crystal hardener is tocopheryl acetate.

6. The sustained release lipid pre-concentrate of claim 1, wherein the weight ratio of component of a) to component b) is 10:1 to 1:10.

7. The sustained release lipid pre-concentrate of claim 1, wherein the weight ratio of a sum of the components of a) and b) to the component of c) is 100:1 to 1:1.

8. A pharmaceutical composition, comprising:
the sustained release lipid pre-concentrate of claim 1; and
a pharmacologically active ingredient selected from among a protein, a peptide, a vaccine, a gene, a non-peptidic hormone, a synthetic chemical drug, and a combination thereof.

9. The pharmaceutical composition of claim 8, wherein the weight ratio of the component of a) to the component of b) is 10:1 to 1:10.

10. The pharmaceutical composition of claim 8, wherein the weight ratio of a sum of the components of a) and b) to the component of c) is 100:1 to 1:1.

11. The pharmaceutical composition of claim 8, which is in a formulation selected from among an injection, an ointment, a gel, a lotion, a capsule, a tablet, a liquid, a suspension, a spray, an inhaler, an eye drop, an adhesive, and a patch.

12. A method for sustained release of a pharmacologically active ingredient, comprising administering the pharmaceutical composition of claim 8 to a mammal, whereby the composition transforms from a liquid state into a liquid crystal gel state in the presence of an aqueous fluid.

13. The method of claim 12, wherein the pharmaceutical composition is administered by a method selected from among injecting, coating, dropping, padding, oral administering, and spraying.

14. The method of claim 12, wherein the pharmaceutical composition is administered by subcutaneous or intramuscular injection.

15. The method of claim 12, wherein the liquid crystals have a non-lamellar phase structure.

16. A pharmaceutical composition, comprising:
the sustained release lipid pre-concentrate of claim 2; and
a pharmacologically active ingredient selected from among a protein, a peptide, a vaccine, a gene, a non-peptidic hormone, a synthetic chemical drug, and a combination thereof.

17. A method for sustained release of a pharmacologically active ingredient, comprising administering the pharmaceutical composition of claim 16 to a mammal, whereby the composition transforms from a liquid state into a liquid crystal gel state in the presence of an aqueous fluid.

* * * * *

UNITED STATES PATENT AND TRADEMARK OFFICE
CERTIFICATE OF CORRECTION

PATENT NO. : 9,526,787 B2
APPLICATION NO. : 14/241696
DATED : December 27, 2016
INVENTOR(S) : Ko et al.

It is certified that error appears in the above-identified patent and that said Letters Patent is hereby corrected as shown below:

In the Specification

At Column 4, beginning at Line 10, please replace the structure of [Chemical Formula 1]

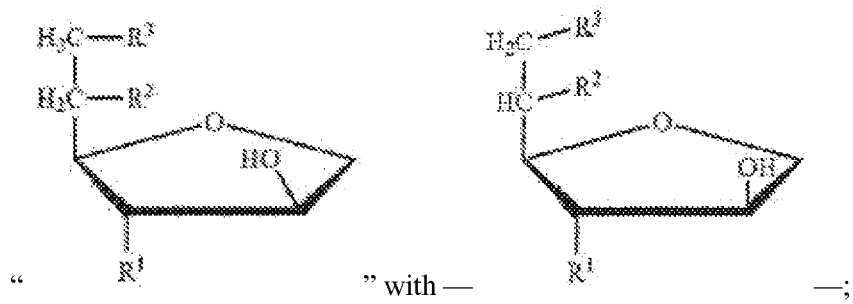

At Column 4, Line 27, please replace "glycerine" with —glyceryl—;

At Column 4, Line 28, please replace "glycerine" with —glyceryl—;

At Columns 3 and 4, please replace the structures in [Chemical Formula 2]

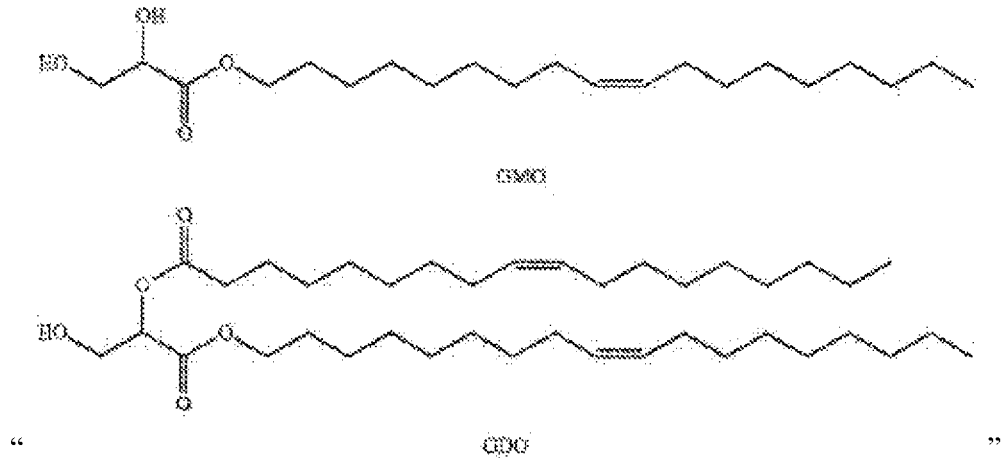

Signed and Sealed this
Fourteenth Day of March, 2017

Michelle K. Lee
*Director of the United States Patent and Trademark Office* with the structures

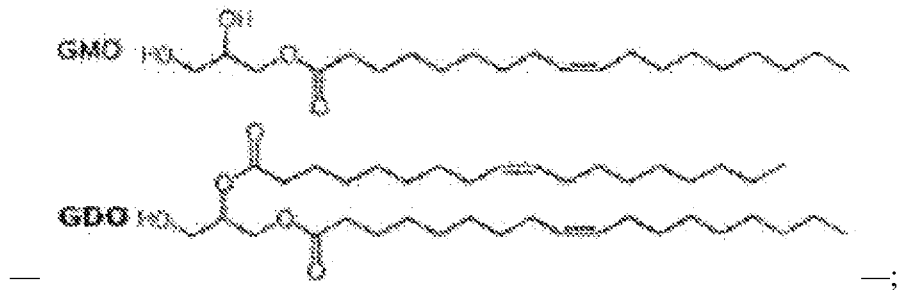

—;

At Column 5, Line 8, please replace "glycerine" with —glyceryl—;

At Column 8, Line 26, please replace "anatrozole" with —anastrozole—;

At Column 12, Line 29, please replace "1×102" with —$1 \times 10^2$—;

At Column 12, Line 31, please replace "CO2" with —$CO_2$—;

At Column 12, Line 34, please replace "CO2" with —$CO_2$—;

At Column 13, Line 33, please replace "5×104" with —$5 \times 10^4$—;

At Column 13, Line 35, please replace "CO2" with —$CO_2$—;

At Column 14, Lines 44-45, please replace "EXPERIMENTAL EXAMPLE" with —Experimental Example—;

In the Claims

Please replace Claim 1 with the following amended claim:
 1. A sustained release lipid pre-concentrate, comprising:
 a) a sorbitan unsaturated fatty acid ester having two or more –OH (hydroxyl) groups on a polar head and having the structure of Formula 1:

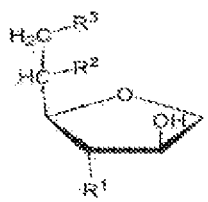
 Formula 1 wherein:
$R^1$ is OH;
$R^2$ is OH or an alkylester of 4 to 30 carbon atoms with one or more unsaturated bonds; and
 $R^3$ is an alkylester of 4 to 30 carbon atoms with one or more unsaturated bonds;
 b) a phospholipid; and c) a liquid crystal hardener selected from the group consisting of triglyceride having a hydrophobic moiety of 15 to 40 carbon atoms, tocopheryl acetate, cholesterol, benzyl benzoate and a mixture thereof, wherein the lipid pre-concentrate exists in a liquid state in the absence of an aqueous fluid and transforms from the liquid state into a liquid crystal gel state in the presence of an aqueous fluid.